United States Patent
Maeda et al.

(10) Patent No.: US 10,499,836 B2
(45) Date of Patent: Dec. 10, 2019

(54) OXYGEN SATURATION MEASURING SENSOR, AND OXYGEN SATURATION MEASURING APPARATUS

(71) Applicant: Fujita Medical Instruments Co., Ltd., Tokyo (JP)

(72) Inventors: Hironobu Maeda, Tokyo (JP); Haruo Yamamura, Tokyo (JP)

(73) Assignee: Fujita Medical Instruments Co., Ltd., Tokyo (JP)

( * ) Notice: Subject to any disclaimer, the term of this patent is extended or adjusted under 35 U.S.C. 154(b) by 418 days.

(21) Appl. No.: 15/117,785

(22) PCT Filed: Apr. 11, 2016

(86) PCT No.: PCT/JP2016/061707
§ 371 (c)(1),
(2) Date: Aug. 10, 2016

(87) PCT Pub. No.: WO2017/179103
PCT Pub. Date: Oct. 19, 2017

(65) Prior Publication Data
US 2018/0110449 A1    Apr. 26, 2018

(51) Int. Cl.
*A61B 5/1455* (2006.01)
*G01N 33/49* (2006.01)
(Continued)

(52) U.S. Cl.
CPC ........ *A61B 5/14552* (2013.01); *A61B 5/1495* (2013.01); *A61B 5/6833* (2013.01);
(Continued)

(58) Field of Classification Search
CPC . A61B 5/14552; A61B 5/1495; A61B 5/6833; A61B 2560/0238;
(Continued)

(56) References Cited

U.S. PATENT DOCUMENTS

2003/0088162 A1*  5/2003  Yamamoto ........... A61B 5/0059
                                                         600/310
2004/0024297 A1*  2/2004  Chen ................... A61B 5/14553
                                                         600/323
(Continued)

FOREIGN PATENT DOCUMENTS

JP        08-322821      12/1996
JP        2004-073559    3/2004
(Continued)

OTHER PUBLICATIONS

Minco_FullFlexDesignGuide_2014 (Year: 2014).*
(Continued)

*Primary Examiner* — Eric F Winakur
*Assistant Examiner* — Abid A Mustansir
(74) *Attorney, Agent, or Firm* — DLA Piper LLP (US)

(57) ABSTRACT

An oxygen saturation measuring sensor is capable of increasing reliability of information of parts having different depth and includes a pad attachable to a human body; plural light sources arranged on the pad to be adjacent in a separate state, and irradiate near-infrared light; plural light receiving elements arranged on the pad to be adjacent in a separate state and correspond one to one to the plural light sources with reference to a common center with an innermost side of the plural light sources, and that receive transmitted light from the corresponding plural light sources; and a ROM unit that stores a reference value through measuring transmitted light using a phantom in advance and stores a light receiving amount of the transmitted light received by the plural light receiving elements.

6 Claims, 9 Drawing Sheets

(51) Int. Cl.
*A61B 5/00* (2006.01)
*A61B 5/1495* (2006.01)

(52) U.S. Cl.
CPC .. *G01N 33/4925* (2013.01); *A61B 2560/0238* (2013.01); *A61B 2560/0412* (2013.01); *A61B 2562/0238* (2013.01); *A61B 2562/043* (2013.01)

(58) Field of Classification Search
CPC .... A61B 2560/0412; A61B 2562/0238; A61B 2562/043; G01N 33/4925
See application file for complete search history.

(56) References Cited

U.S. PATENT DOCUMENTS

| | | | |
|---|---|---|---|
| 2008/0058638 A1 | 3/2008 | Zhu et al. | |
| 2010/0130840 A1* | 5/2010 | Isaacson | A61B 5/14553 600/323 |
| 2010/0331640 A1* | 12/2010 | Medina | A61B 5/14535 600/324 |
| 2011/0137177 A1 | 6/2011 | Toma et al. | |
| 2011/0268362 A1 | 11/2011 | Toma et al. | |
| 2013/0102907 A1* | 4/2013 | Funane | A61B 5/0075 600/476 |
| 2018/0220968 A1* | 8/2018 | Funane | A61B 10/00 |

FOREIGN PATENT DOCUMENTS

| | | |
|---|---|---|
| JP | 2007-518443 | 7/2007 |
| JP | 2008-064675 | 3/2008 |
| JP | 3183811 | 5/2013 |
| JP | 2016-000240 | 1/2016 |
| WO | 2010/143421 | 12/2010 |
| WO | 2011/027548 | 3/2011 |

OTHER PUBLICATIONS

Notice of Reasons for Refusal dated Sep. 6, 2016, of corresponding Japanese Application No. 2016-543205, along with an English translation.

* cited by examiner

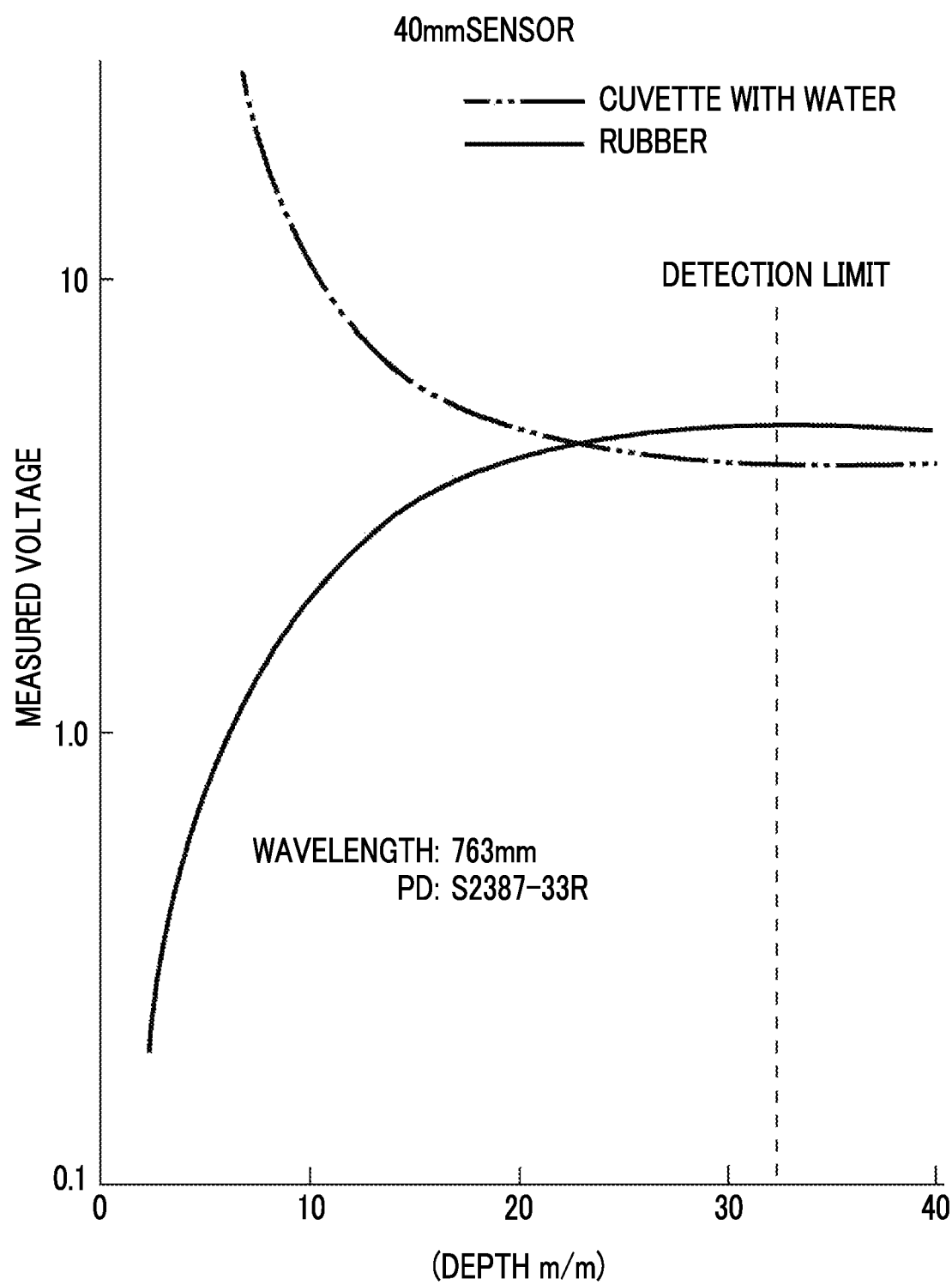

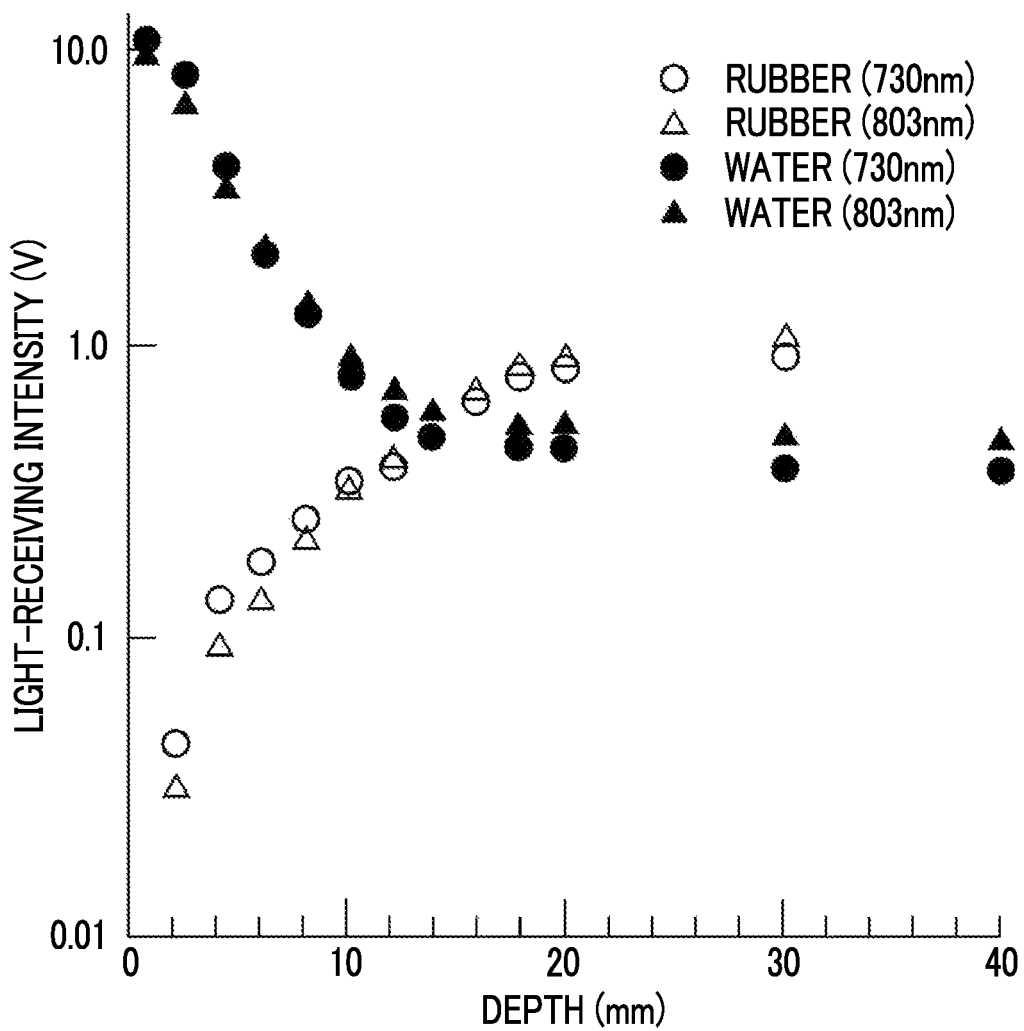

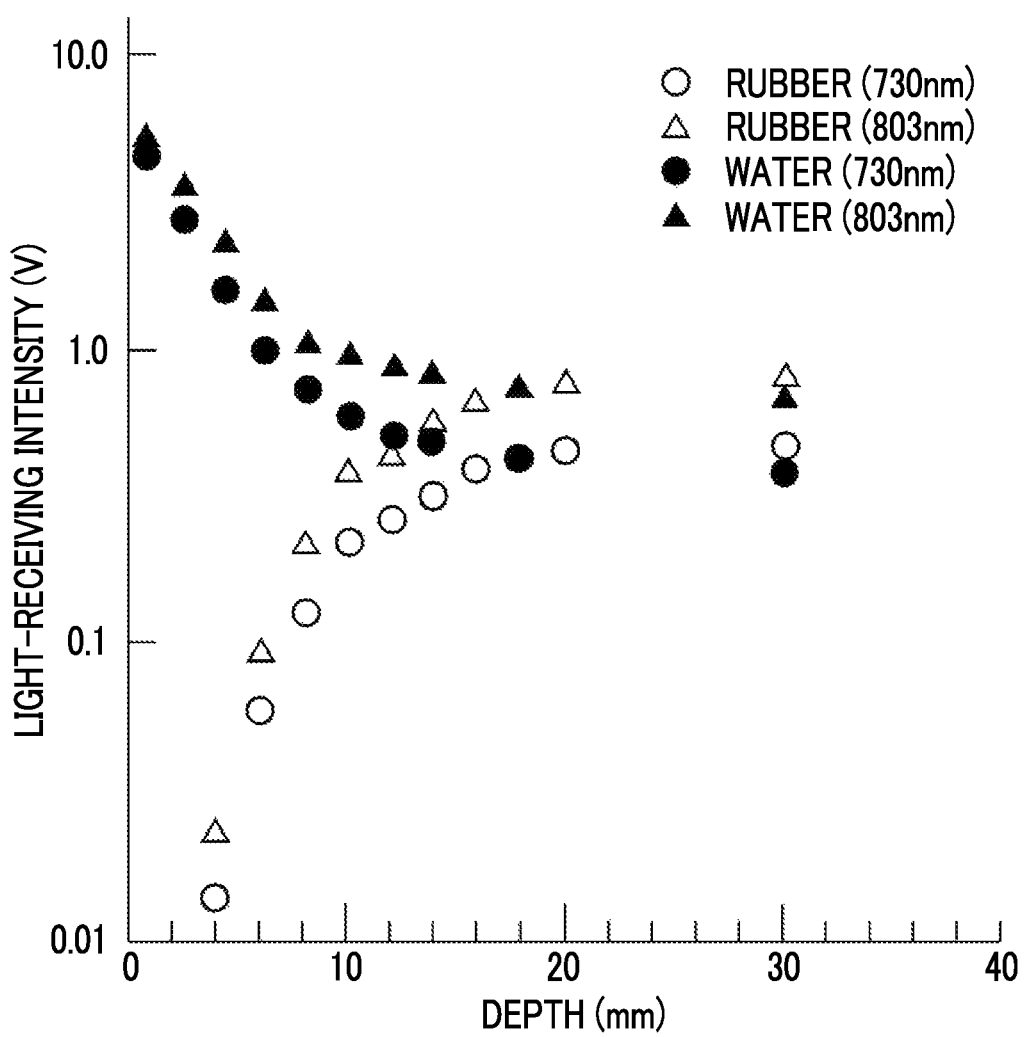

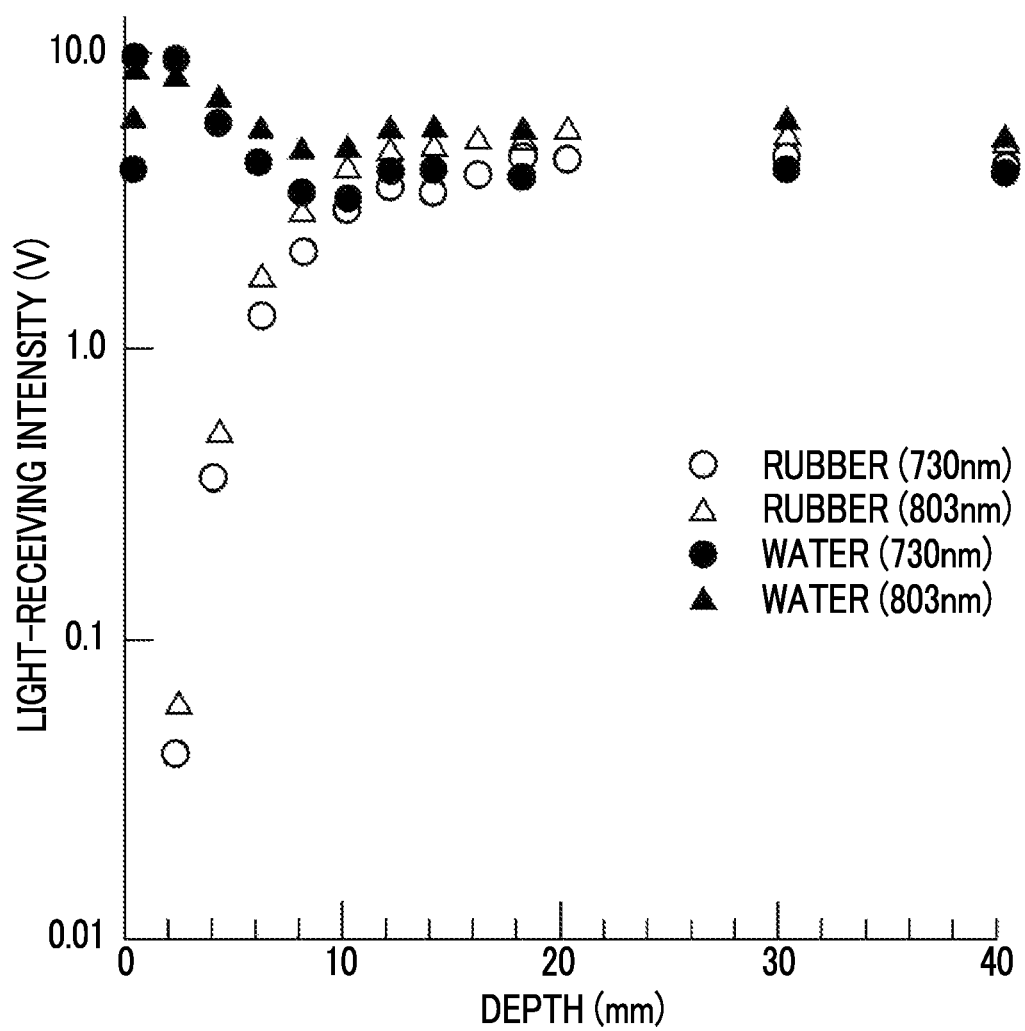

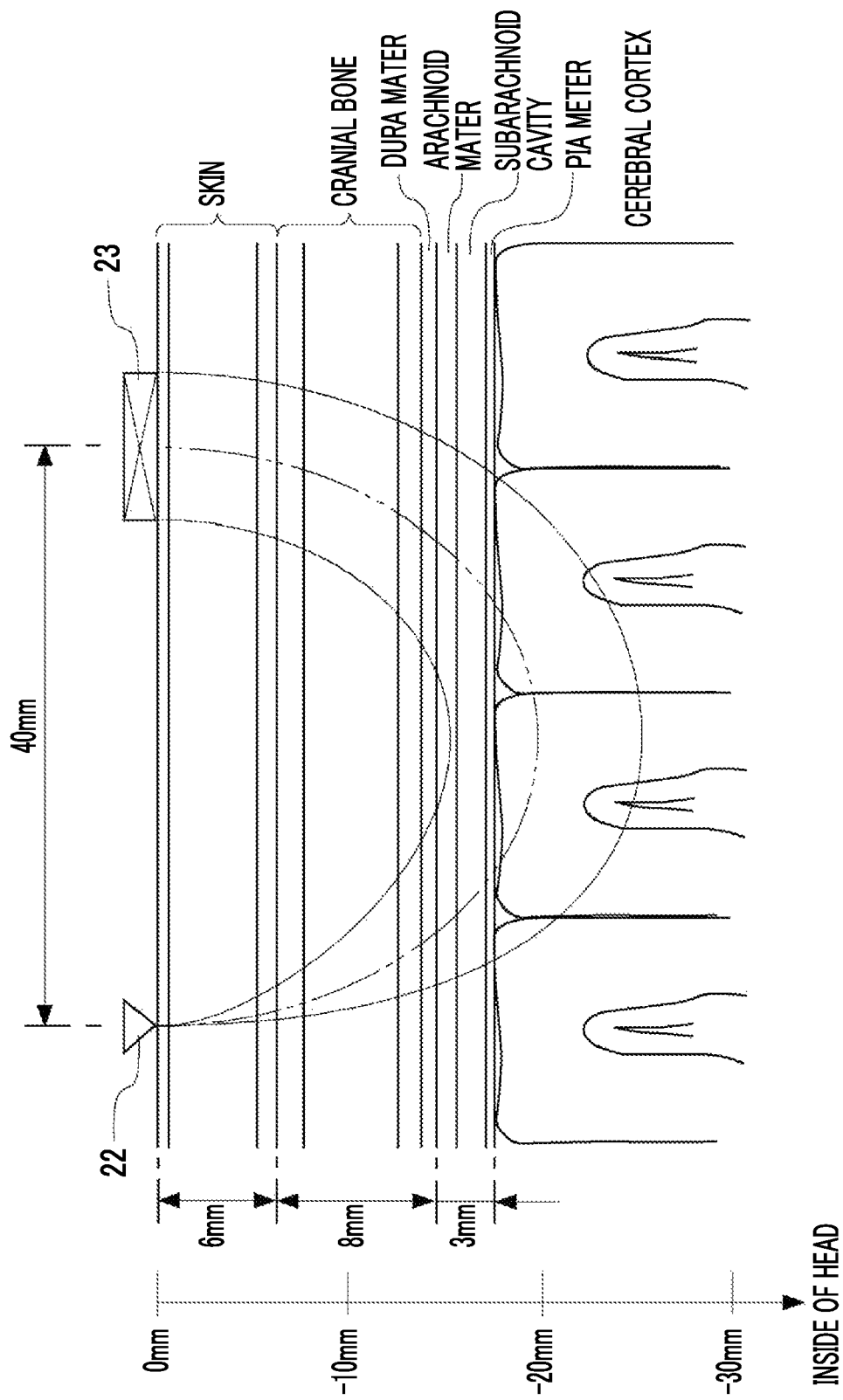

OXYGEN SATURATION MEASURING SENSOR, AND OXYGEN SATURATION MEASURING APPARATUS

TECHNICAL FIELD

This disclosure relates to an oxygen saturation measuring sensor, and an oxygen saturation measuring apparatus and, in particular, an oxygen saturation measuring sensor, and an oxygen saturation measuring apparatus that non-invasively measures oxygen saturation in blood inside a living body using near-infrared light.

BACKGROUND

Supply of oxygen based on breathing of a human body as a living body is achieved through transportation and exchange by circulating blood. Oxygen taken in by breathing is combined with hemoglobin (Hb) in the blood by gaseous exchange at alveoli. The oxygen taken into the blood is transported to the whole body through arterial blood, and is taken into cells through capillaries.

Since cells of respective parts live using oxygen in the blood, it is desirable to measure the oxygen condition of the cranium, in particular, the cerebral cortex in real time, and check the state of the brain cells constantly during in particular cardiac surgery or cardiac massage due to cardiac arrest.

As a method of measuring the oxygen condition of the cerebral cortex, an oxygen saturation measuring apparatus is known that non-invasively measures oxygen saturation in blood inside a living body using near-infrared light by attaching a pad onto a head of a human body (with reference to Japanese Patent Application Laid-Open Publication No. 2016-000240, for example).

In the aforementioned conventional sensor, one light source and two light detectors are used, information of a deep part of a head of a human body is obtained by subtracting information of a shallow part thereof from the information of the deep part thereof. At that time, a center (line) based on a clearance between the light source and one of the light detectors and a center (line) based on a clearance between the shared light source and the other one of the light detectors are misaligned.

Thus, since the center for the deep part and the center for the shallow part are different in the region passing through the near-infrared light, it is hard to say that accurate information of only the deep part is obtained on the basis of those parts in which arrangements of blood vessels are different in a living body, which raises the problem of low reliability.

It could therefore be helpful to provide an oxygen saturation measuring sensor and an oxygen saturation measuring apparatus capable of improving reliability of information of parts having different depth.

SUMMARY

We thus provide an oxygen saturation measuring sensor including: a pad attachable to a human body; plural light sources arranged on the pad to be adjacent in a separate state, and irradiate near-infrared light; plural light receiving elements arranged on the pad to be adjacent in a separate state and correspond one to one to the plural light sources with reference to a common center with an innermost side of the plural light sources, and that receive transmitted light from the corresponding plural light sources; and a ROM unit that stores a reference value through measuring transmitted light using a phantom in advance and stores a light receiving amount of the transmitted light received by the plural light receiving elements.

Since the centers (centerlines) of clearances between the respective plural light sources and the one-to-one corresponding plural light receiving elements are identical, it is possible to improve reliability of information of parts having different depth.

BRIEF DESCRIPTION OF THE DRAWINGS

FIG. 2A is an illustration diagram of a pad in which one light source and two light receiving elements are arranged. FIG. 2B is an illustration diagram of a pad in which two pairs each of which contains a light source and a light receiving element are laterally arranged. FIG. 2C is an illustration diagram of a pad in which plural light sources and plural light receiving elements having one-to-one correspondence to each other with respect to the same center (line) are arranged.

FIG. 3 is a graph showing the relationship between measured voltage and measured depth using a cuvette with water and rubber when the clearance is set at 40 mm.

FIG. 4 is a graph showing the relationship between a light-receiving intensity and measured depth using a cuvette with water and rubber when the clearance is set at 40 mm.

FIG. 5 is a graph showing the relationship between a light-receiving intensity and measured depth using a cuvette with water and rubber when the clearance is set at 30 mm.

FIG. 6 is a graph showing the relationship between a light-receiving intensity and measured depth using a cuvette with water and rubber when the clearance is set at 20 mm.

FIG. 7A is an illustration diagram of no following capability type to a curved surface. FIG. 7B is an illustration diagram of a following capability type to a curved surface.

FIG. 8 is an illustration diagram showing the relationship between a cross-sectional configuration of a head of a human and sensitivity of a sensor.

DESCRIPTION OF REFERENCE NUMERALS

2: Sensor unit (oxygen saturation measuring sensor)
21: Pad
22: Light sources (22A, 22B)
23: Light receiving elements (23A, 23B)
24: ROM
3: Main body
3E: Arithmetic processing unit

DETAILED DESCRIPTION

Hereinafter, a description will be given for an example of our sensors and apparatus with reference to the Drawings.

Figure 1:
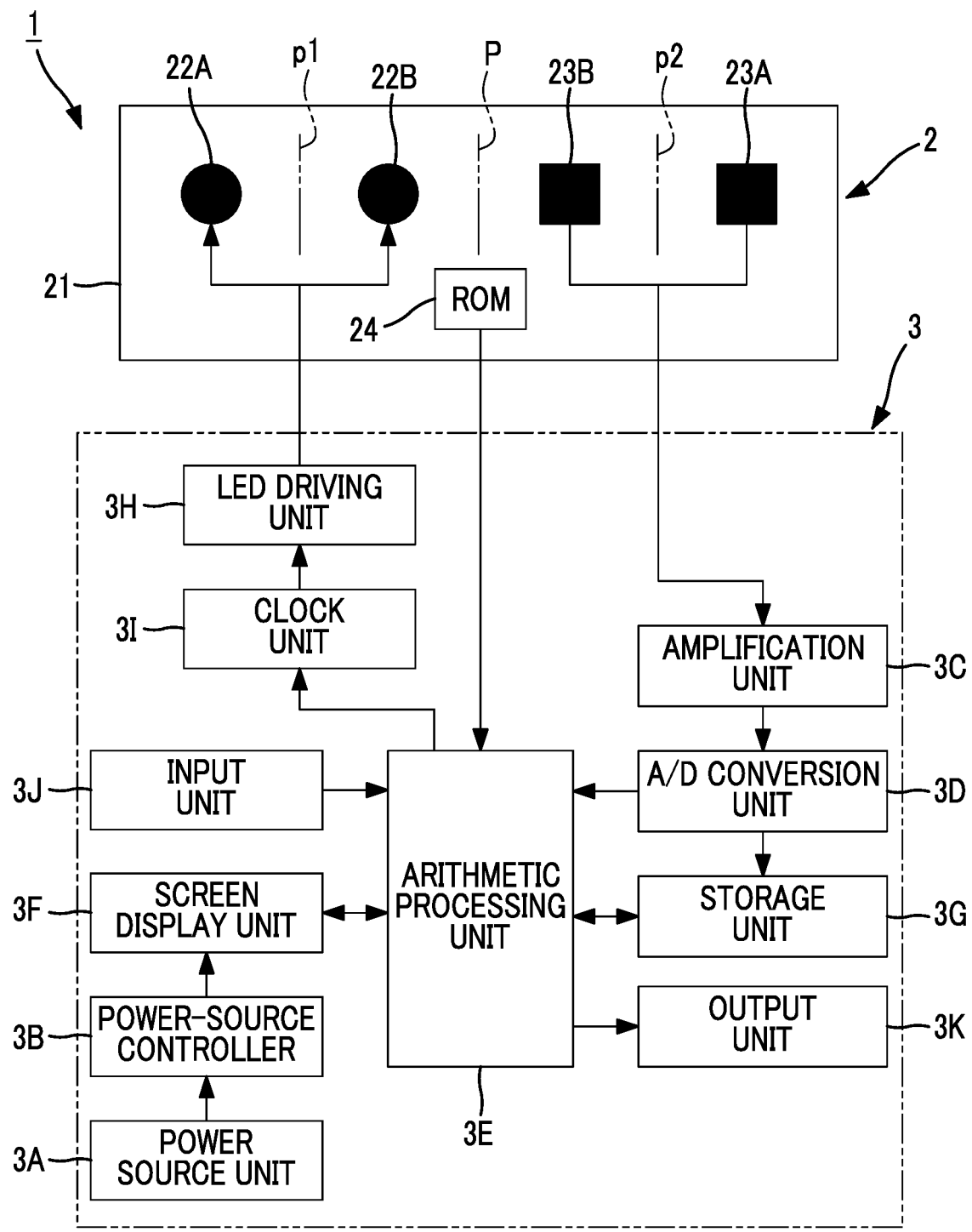
FIG. 1 is a block diagram of an oxygen saturation measuring apparatus according to an example.

As shown in FIG. 1, an oxygen saturation measuring apparatus 1 includes a sensor unit 2 to be put onto, for example, a surface of a cerebral cortex, and a main body 3.

The sensor unit 2 includes: a pad 21 attachable to a human body; plural light sources 22A and 22B (hereinafter, also referred to as "light sources 22") arranged on the pad 21 to be adjacent to each other in a separate state, and irradiate near-infrared light; plural light receiving elements 23A and 23B (hereinafter, also referred to as "light receiving elements 23") arranged on the pad 21 to be adjacent to each other in a separate state and correspond one to one to the plural light sources 22A and 22B with reference to a common center P with the light source 22B on the innermost side of the plural light sources 22A and 22B, and that receive transmitted light from the corresponding plural light sources 22A and 22B; and a ROM portion 24 that stores a reference value through measuring transmitted light using a phantom in advance.

As for the plural light sources 22A and 22B and the plural light receiving elements 23A and 23B, the light source 22A and the light receiving element 23A correspond one to one to each other, and the light source 22B and the light receiving element 23B correspond one to one to each other. Note that, in the description to be given below, the combinations of the light sources (22A and 22B) and the light receiving elements (23A and 23B) are also referred to as simply "sensors". In this case, particularly the combination of the light source 22A and the light receiving element 23A is also referred to as "a sensor A", and the combination of the light source 22B and the light receiving element 23B is also referred to as "a sensor B".

The plural light sources 22A and 22B and the plural light receiving elements 23A and 23B are arranged so that the plural light sources 22A and 22B are separately located on one side of the center P at an equal distance and the plural light receiving elements 23A and 23B are separately located on the other side of the center P at an equal distance. Further, the center p1 of the clearance (center distance) between the light source 22A and the light source 22B and the center p2 of the clearance (center distance) between the light receiving element 23A and the light receiving element 23B are located on symmetrical positions with respect to the center P.

Accordingly, the light source 22A and the light source 22B, the light source 22B and the light receiving element 23B, and the light receiving element 23A and the light receiving element 23B are arranged to have the clearances (center distances) equal to each other. In this case, the clearance between the light source 22A and the light receiving element 23A, which is large distance, is set to obtain information at a deep part of a cranium (for example, 40 mm). Meanwhile, the clearance between the light source 22B and the light receiving element 23B, which is small distance, is set to obtain information at a shallow part of a cranium (for example, 20 mm). Note that the expressions deep and shallow in the example are used in a comparison between two pairs of sensors. Further, for example, when three or more pairs of sensors are arranged, they are configured to obtain information of the deepest part, information of the shallowest part, and information of one or more intermediate depth parts equally dividing the region between the deepest part and the shallowest part. Note that the distances between the light sources 22A and 22B and the light receiving elements 23A and 23B are set to be changed depending on sizes, thicknesses and the like of craniums such as applications to adults, children (children to young adults), and infants.

The light source 22A and the light source 22B use LEDs, and irradiate near-infrared light having a predetermined wavelength at pulses of 0.2 msec per wavelength for 10 times per second, for example. The light receiving element 23A and the light receiving element 23B use photodiodes, and are configured to detect the near-infrared light having wavelengths corresponding to oxyhemoglobin, deoxyhemoglobin, and a cross-point thereof, and calculate measured values by amplifying the obtained signals. Thus, the light source 22A and the light source 22B have wavelength characteristics as absorption spectrum characteristics of near-infrared light, in which 805 nm where absorbance of oxyhemoglobin and absorbance of deoxyhemoglobin approximately coincide with each other, 770 nm lower than that, and 870 nm larger than that are set.

Note that, as a role of the wavelengths, the wavelength of 770 nm and the wavelength of 870 nm are used in combination, as a ratio R/IR to calculate oxygen saturation. The wavelength of 805 nm is used when the total amount of hemoglobin and concentration change are measured. In other words, the wavelength of 805 nm is where absorbance coefficient of oxyhemoglobin and absorbance coefficient of deoxyhemoglobin in human are equal, correlates with the total amount of hemoglobin or concentration thereof independently of oxygen saturation and, accordingly, is used as an index of the amount of blood as a hemoglobin index. By this configuration, when oxygen saturation is measured, oxygen saturation from low level to high level can be measured with accuracy from R/IR by using the two wavelengths of 770 nm and 870 nm at which the absorbance coefficient of oxyhemoglobin and the absorbance coefficient of deoxyhemoglobin in human are inversed while the wavelength of 805 nm at which the absorbance coefficients are equal is interposed.

When the pad 21 is mounted onto a surface of a cranium, the intensity of light decreases in inverse proportion to a square of each of the distances from the light source 22A to the light receiving element 23A and from the light source 22B to the light receiving element 23B, as the distances thereof are increased. If the intensity of light is weak, the light passes through the scalp at a shallow part of the cranium and the periphery of the cranial bone, while the light reaches the cerebral cortex at a deep part in the cranium as the intensity thereof is stronger.

The main body 3 forms a circuit connection to the sensor unit 2, and is configured by a power source unit 3A, a power-source controller 3B that controls voltage of the power source unit 3A, an amplification unit 3C that amplifies measured data, an A/D conversion unit 3D that converts data into digital signals for calculation, an arithmetic processing unit 3E that calculates the data, a screen display unit 3F that displays the data, a storage unit 3G that stores the data, a LED driving unit 3H that controls driving of the LEDs as the power sources 22A and 22B of the sensor unit 2, a clock unit 3I configured to synchronize pulse signals with respect to the LED driving unit 3H, an input unit 3J configured to make an operation from the outside, and an output unit 3K that outputs the data to the outside by wire (for example, a USB) or wireless.

Upon a switch operation to the power source unit 3A, the main body 3 instructs the LED driving unit 3H to emit light and receive light through the arithmetic processing unit 3E. Then the light of the predetermined wavelength is output from the two power sources 22A and 22B of the sensor unit 2 while the intensity thereof is changed to be strong or weak, and transmitted light of the light is received by the corresponding two light receiving elements 23A and 23B.

A reception signal received by each of the light receiving elements 23A and 23B is amplified by the amplification unit 3C, the signal thus amplified is converted into a digital signal by the A/D conversion unit 3D, and supplied to the arithmetic processing unit 3E. The arithmetic processing unit 3E calculates oxygen saturation rSO2 and the like in real time using the Beer-Lambert law with these light emission signals and the light reception signals, and the calculation results are stored in the storage unit 3G, and displayed on the screen display unit 3F. Specifically, the arithmetic processing unit 3E measures oxygen saturation rSO2 of intracerebral blood and a hemoglobin index HbI.

A description will be given for when the measuring apparatus having the aforementioned configuration is used. First, the two light sources 22A and 22B and the light receiving elements 23A and 23B of the sensor unit 2 are mounted onto a surface of a cranium while being in contact therewith. Then, a signal of light is output to the light sources 22A and 22B, and irradiation to the inside of the cranium is performed. Subsequently, transmitted light through the cranium is received by the light receiving elements 23A and 23B to obtain respective light receiving signals. The light receiving signals after being subjected to scattering and reflection by the blood and mainly by hemoglobin can be obtained with high accuracy. After that, arithmetic processing is performed by the arithmetic processing unit.

The measuring apparatus 1 irradiates near-infrared light to the cranium, and measures oxygen saturation and concentration change of hemoglobin in a limited region inside the brain using the "Beer-Lambert law" defining that the absorption amount of light is proportional to incident light and concentration of solute. By using the difference between the light absorption spectrums of oxyhemoglobin and deoxyhemoglobin, absorbance is calculated from the light of different wavelengths (770 nm, 870 nm) passing through the cranium and detected by the light receiving elements, and oxygen saturation (rSO2) of the limited region is calculated.

Information obtained by the sensors is information of all light passages between the respective light sources (22A, 22B) and the corresponding light receiving elements (23A, 23B) as pairs, and if the centers are different, evaluation as the information of the center of the sensor is not accurately performed, or the information has low reliability. In particular, since the blood configuration is different depending on regions of a living body, the difference is out of the negligible range.

For example, when the clearance in the sensor A is set at 40 nm and the clearance in the sensor B is set at 20 mm, the sensor A reflects information of a cranium at the depth of up to around 32 mm while the sensor B reflects information of the cranium at the depth of up to around 16 mm. Thus, the arithmetic processing unit 3E is capable of obtaining information of the cranium from the depth of around 16 mm as a shallow part to the depth of around 40 mm as a deep part, by subtracting the information of the sensor B from the information of the sensor A.

Figure 2A:
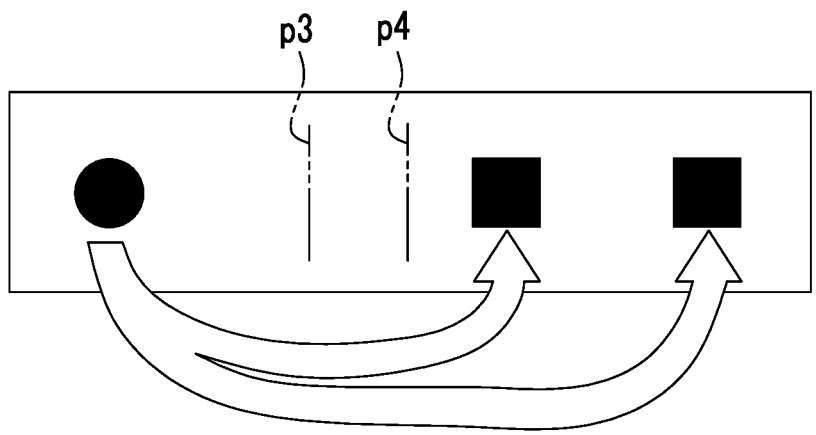
FIGS. 2A, 2B and 2C show another oxygen saturation measuring sensor according to an example.

In this case, the already-known configuration in which the centers (centerlines) between the one light source and the respective two light receiving elements are different as shown in the related art has the one light source as shown in FIG. 2A. Thus, when the clearance between the light source to the farther one of the light receiving elements is set at 40 mm equally to the sensor A and the clearance between the light source to the closer one of the light receiving elements is set at 20 mm, it is difficult to say that information at the same position of the cranium at different depth is accurately obtained since the centers p3 and p4 are misaligned by 10 mm and the reliability thereof is low.

It has been known that the depth of a part to be measured can be varied, through an experiment in which the clearance in the sensor A and the clearance in the sensor B are made to be changed. In other words, since light flux outputting from the light source (22A, 22B) instantly becomes scattering light, there are different light passages from the light source (22A, 22B) to the light receiving element (23A, 23B) (for example, referred to as a shape of banana in the Monte-Carlo simulation). Typically, the deepest part where the light passes corresponds to a position around a peak of an isosceles triangle. From the above, the light receiving element of the sensor B is located just above the peak of the sensor A (clearance of 40 mm), which is different from the center (line) of the sensor B. To accurately obtain information at the shallow part just above the deep part by the sensor having the clearance of 40 mm, it is necessary to make the center of the sensor having the clearance of 20 mm coincide with the center of the sensor having the clearance of 40 mm. As described above, plural sensors having different clearances are located such that, for example, the sensor B having the clearance of 20 mm is located within the sensor A having the clearance of 40 mm, and the centers thereof are set to coincide with each other, which is capable of accurately measuring information at the shallow part just above the deep part and, accordingly, obtaining accurate information compared to information only at the deep part.

The result obtained by subtracting the sensor B from the sensor A indicates information only at the deep part of the cranium. However, since it is better to know the whole of the cranium including the shallow part, measurements are performed individually for the clearance of 40 mm set to target the deep part and the clearance of 20 mm set to target the shallow part, as channels for measurement. To obtain the information only at the deep part, it is preferable to separately calculate the difference between the information of 40 mm and the information of 20 mm. Note that, only information at the deep part is obtained in the conventional method in which the one light source and the two light receiving elements are used.

Confirmatory experiment data of measured depth according to the clearance of the sensor is shown in FIGS. 3 to 6. Among these experimental examples, FIGS. 3 and 4 show an example when the deep part of the cranium is targeted by setting the clearance of 40 mm. In this example, experiment data is shown when a black rubber sheet and a cuvette filled with water (to be described later) are placed under the sensor and a confirmation how deep the detection signal is detected is made. From the result, we confirmed that the detection limit of the depth is from 28 mm to 32 mm when the clearance between the light source and the light receiving element is set at 40 mm (FIGS. 3 and 4). In the similar manner, we concluded that the depth from 70% of the clearance between the light source and the light receiving element to 80% of the clearance therebetween at the maximum is detectable for each of the clearances of 30 mm (FIG. 5) and 20 mm (FIG. 6).

Figure 2B:
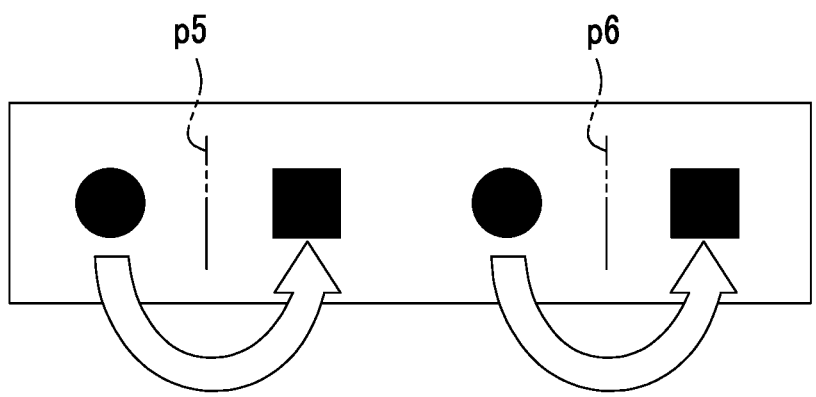
Figure 2C:
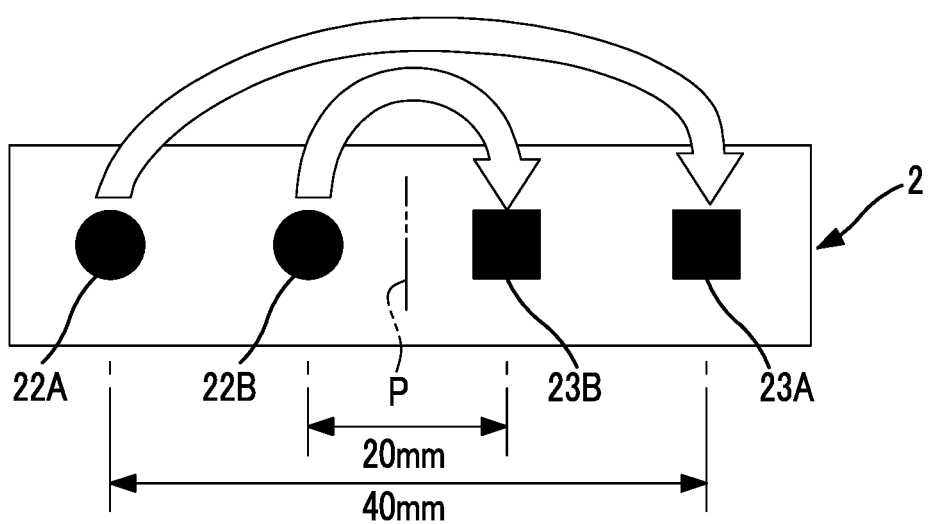

Thus, as shown in FIG. 2C, light sources 22A and 22B and corresponding light receiving elements 23A and 23B are configured as two pairs, and the sensor A (light source 22A and the light receiving element 23A) is configured to have the clearance of 40 mm while the sensor B (light source 22B and the light receiving element 23B) is configured to have the clearance of 20 mm. Further, the irradiation and reception of light in each pair are alternately operated, and thereby information at up to the deep part of the cranium is configured to be obtained by the sensor A, and information at the shallow part of the cranium is configured to be obtained by the sensor B. Since the two pairs as the sensor A and the sensor B have the same center (centerline P), information at the same measurement position having different depth can be independently obtained. If the information at the shallow part is subtracted from the information at the deep part, information only at the deep part is obtained. Note that, the same measurement position is not strictly interpreted as the same measurement position because of the different depth. However, since the sensor A and the sensor B provided in the pad 21 have the same center (centerline P), the same measurement position is to be substantially understood as the meaning of measurement in which the detection target is located just below the periphery of the center thereof.

Thus, the cases in which the centers p3 and p4 are misaligned as shown in FIG. 2A and the centers p5 and p6 are misaligned because of the sensor configurations arranged separately on the right and left as shown in FIG. 2B do not indicate "the same measurement position". In each of the configurations of FIG. 2A to 2C, the information obtained from the light when the cranium is set as the target becomes information of solvent in a part where the light from the light source to the light receiving element passes through the inside of the cranium, but information of a part where the light does not pass through the inside of the cranium is not reflected.

Since the light passage where the light reaches the light receiving element from the light source is considered to have a shape referred to as a banana shape by the Monte-Carlo simulation, the farthest part becomes a peak of a regular triangle formed by connecting the light source, the light receiving element, and the inside of the cranium, and coincides with the center (centerline P) of the clearance between the light source and the light receiving element.

Figure 7A:
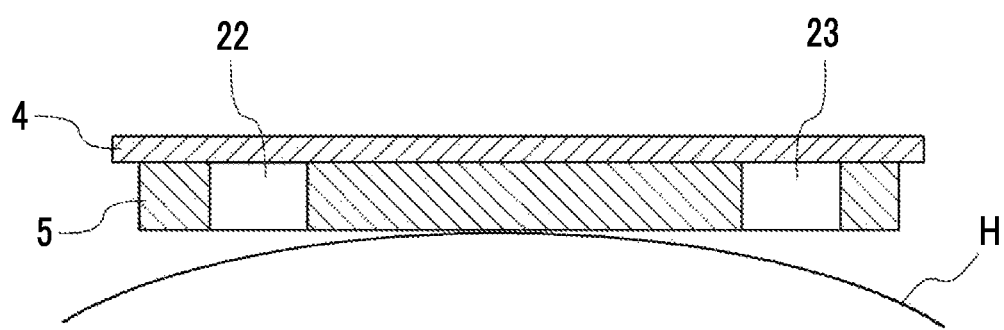
FIGS. 7A and 7B show schematic configurations of the pad.

A description will be given for the configuration of the pad 21. The pad 21 has an attachment region basically formed to curve when a cranium is an attachment target. Thus, as shown in FIG. 7A, the printed substrate 4 is adopted for mass production, and the light source 22 and the light receiving element 23 are placed and soldered on the surface of the substrate 4. Further, since the surfaces of the light source 22 and the light receiving element 23 are away from the printed substrate 4 by the thicknesses of respective components, the surfaces of the components are treated with foamed rubber 5 to have a flat surface entirely. In this case, it becomes essential that the components are brought into close contact with a living body H. In other words, the light is not detectable unless the light emitting surface and the light receiving surface of the respective components are directed upward with respect to the printed substrate 4, and in addition, since the living body H has a curved surface, the components are difficult to be brought into close contact with the curved surface of the living body H, which causes measurement error due to mixture of outside light.

Figure 7B:
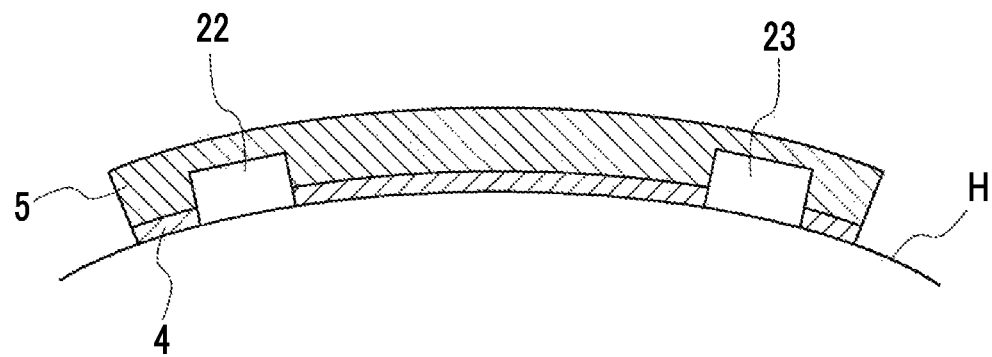

To avoid this, as shown in FIG. 7B, holes having the sizes identical to the light source 22 and the light receiving element 23 are formed in the printed substrate 4 when the light source 22 and the light receiving element 23 are mounted thereto so that the light source 22 and the light receiving element 23 have the same plane as a base surface (surface with copper foil) of the printed substrate 4, and the foamed rubber 5 is provided on the back surface side of the printed substrate 4. Accordingly, following capability (adhesiveness) to the curve of the living body H is secured, and stable measurement result can be obtained.

Next, a description will be given for a measurement example in which the shallow part and the deep part are individually measured to obtain information from the deep part to the shallow part inside a cranium, with reference to FIG. 8.

The sensor unit 2 is capable of measuring the amount of hemoglobin and oxygen saturation in blood inside a living body H by using near-infrared light. From the aforementioned experimental result, the sensor has monitorable depth that is 70% to 80% of the clearance. FIG. 8 shows that a cranial bone of adults has the thickness of 8 mm to 10 mm or so, and the thickness from the scalp to the cranial bone is from 5 mm to 8 mm or so.

To measure only information of outside of a cranium, it is only necessary to measure information at depth 13 mm to 18 mm. Thus, when the monitorable range is 70% to 80%, the clearance in the sensor is 18.5 mm to 25.7 mm, or 16.2 mm to 22.5 mm. Then, we believe that information of inside of a cranium is not included if the distance between light emission and light reception is 20 mm by taking into account the thickness of the cranial bone (8 to 10 mm).

Thus, information obtained by the sensor having the clearance of 40 mm includes information of the outside and inside of the cranium, as shown in FIG. 8. The information of only the inside of the cranium is believed to be obtained by subtracting the information of the outside of the cranium obtained by the light emission and light reception at 20 mm, from the information obtained at the clearance of 40 mm.

From the experimental result, when elements having the same characteristics are used, a signal of the light receiving element (23A) of the sensor having the clearance of 40 mm is largely affected by absorption and scattering compared to the signal of the light receiving element (23B) of the sensor having the clearance of 20 mm. Thus, the amplification factor needs to be increased 40 times or so. From the above, when a calculation is performed with the absorption amount by hemoglobin, the absorption amount at 20 mm of the clearance is subtracted from the absorption amount at 40 mm of the clearance because the absorption amount at 40 mm of the clearance is larger, and then the ratio R/IR is calculated. Thereby, oxygen saturation at only the deep part is calculated.

When a blood flow only at a muscle or the like is intended to be evaluated by deleting information at a shallow part up to a fatty layer under skin instead of information of the inside of the cranium, combination of 10 mm of the clearance and 30 mm of the clearance is the best to achieve the most appropriate measurement of the blood flow of the muscle by taking into account the distance to the muscle in the depth direction that is 12 to 20 mm, the thickness between the skin and the fatty layer that is 6 mm and the like.

Specifically, the absorption amount $K\lambda$ is obtained by Log 10 (1000/measured voltage), and thus the measured voltage at 40 mm of the clearance is directly used, and the measured voltage at 20 mm of the clearance is multiplied to be 40 times as the amplification factor, and difference therebetween are set as the deep part of the cranium. Note that 1000 in the aforementioned formula Log 10 (1000/measured voltage) is incorporated into this calculating formula on the basis of the experimental result in which the voltages of the light sources (22A and 22B) are back calculated by a logarithmic chart with the measured voltages of the light receiving elements (23A, 23B), and correspond to 1000 times thereof. The absorption amount at the deep part is obtained by $KD = \log 10 (1000/40 \text{ mm}) - \log 10 (1000/(20 \text{ mm} \times 40))$.

Oxygen saturation is obtained from the ratio R/IR using the aforementioned theory with the absorption amount thus calculated. The hemoglobin index is obtained so that the absorption amount is directly used as a relative value and correlates with HbI. As described above, the center positions are aligned, the upper side in the depth direction is independently obtained, and thereby information of a blood flow in a target region other than a cranium is selectively obtained if this method is applied to other regions.

Next, a description will be given for a method of obtaining a calibration curve. When oxygen saturation of blood in a living body and a reference to measure change of the amount of blood are non-invasively evaluated with accuracy, it is preferable that the blood having oxygen saturation having already been known accurately is measured, the same blood is also measured by a CO oximeter, and consistency between the value of each apparatus and the value of the CO oximeter is accurately evaluated.

At this time, when the blood is adjusted to have any oxygen saturation, the blood is brought into contact with air to increase the oxygen saturation of the blood, or the blood is reduced with sodium dithionite ($Na_2S_2O_4$) as a reducing agent to decrease the oxygen saturation of the blood, for example. Further, since light is absorbed due to high concentration of hemoglobin in a whole blood state, the blood (whole blood) is diluted with saline by 3 times (note that the maximum percentage of blood vessels in the living body is owned by cerebral blood vessels, and is calculated as approximately 30%). The blood in the brain exists in capillary blood vessels and the like, the condensation per whole tissues is 54 ml/min or so with respect to 100 grams of brain tissues, and thus condensation of hemoglobin per whole tissues is approximately 5 grams/dl or so. In the aforementioned measurement, the blood diluted with heparin-added saline to occupy approximately one third is used.

If tonometered blood having a known oxygen saturation is prepared to measure oxygen saturation, a calibration curve can be prepared with the blood for calibration of the sensor. An element identical to the actual sensor is used to measure voltage of light receiving signals for two different wavelengths with respect to a cuvette filled with the tonometered blood and having the thickness of approximately 1 mm, and light absorption amounts are calculated from the measured voltage on the basis of the Beer-Lambert law. If respective ratios (R/IR) of the light absorption amounts are obtained for corresponding oxygen saturation of the tonometered blood, the calibration curve of relation between the oxygen saturation and R/IR can be set by connecting points of R/IR.

Figure 9A:
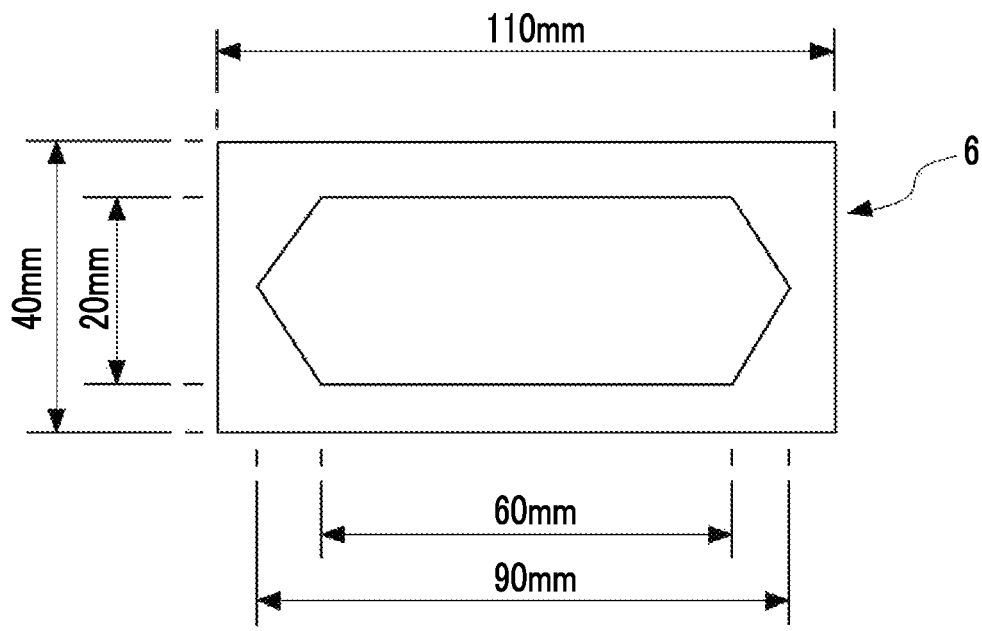
FIG. 9A is an illustration diagram of a cuvette used when a calibration curve is formed.

The measurement of the ratio of light absorption R/IR is conducted by the sensor such that the cuvette 6 shown in FIG. 9 is filled with the tonometered blood (upon confirmation by measuring oxygen saturation and concentration of hemoglobin using a CO oximeter) and a light absorption characteristic for each light wavelength is measured by the sensor having the light source 22 at the same wavelength to be used and the light receiving element 23 in a blacked-out state in which outside light is blocked out.

Figure 9B:
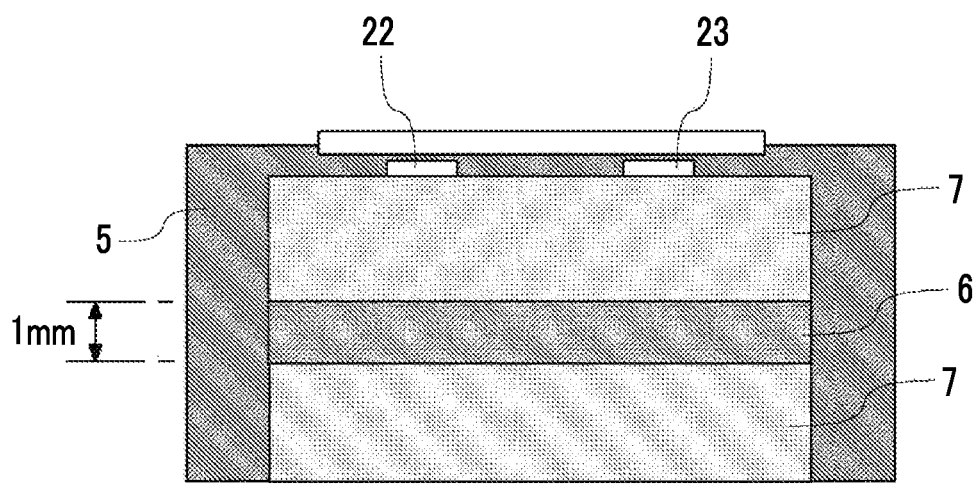
FIG. 9B is an illustration diagram of a phantom used when the calibration curve is formed.

As shown in FIG. 9B, the cuvette 6 is placed just below the sensors 22 and 23, and the upside and downside of the cuvette 6 are held with a ham 7 or the like as an imitation of a living body for use. The tonometered blood is prepared such that oxygen saturation is finely defined from 0% to 100%, and a calibration curve is made from the respective measurement results. By the measurement of oxygen saturation as described above, practical and reproducible measured values are set instead of identical values.

Other Conditions

The blood is used to measure reference oxygen saturation with the cuvette 6 having the thickness of around 1 mm. Oxygen saturation of the blood inside the cuvette 6 is confirmed by the CO oximeter, before and after the measurement. The oxygen saturation is 0% to 100% at intervals of 5%, and measurement is conducted for 10 times or more for each oxygen saturation. From the measurement results thereof, the ratio R/IR is calculated at each wavelength, and a correlation curve with oxygen saturation by the CO oximeter is prepared. The sensor element to be used satisfies the specification same as that for actual goods or apparatus to be evaluated. The wavelengths to be used are set at 770 nm, 805 nm, and 870 nm, as mentioned above.

Next, a description will be given for a configuration example of a phantom to determine the reference values. The reference values in this case are reference values of oxygen saturation and the amount of hemoglobin in blood in a living body in a non-invensive state, and are needed to be set as reference values to accurately evaluate blood information in the living body.

It is commonly known that the living body is a high scattering substance with respect to light. Although the scattering coefficient and diffusion coefficient are measureable, it is difficult to constantly maintain a certain state because the living body changes at every moment. There are some resins having the same degree of scattering, diffusion, and optical characteristics as the living body, and thus the phantom which is made of a chosen material having the same optical characteristics as the living body and in which multiple layers are overlapped similarly to the living body is configured.

Configuration of Phantom (Calibration Device)

The phantom is made to have optical characteristics approximately identical to, for example, those of an area from forehead to a cranium and cortex of an adult, by alternately combining resin sheets having similar scattering and absorption characteristics to a living body. The actual configuration is:

one absorption sheet on the surface 0.5 t;
five scattering sheets therebelow 2 t;
one absorption sheet therebelow 0.5 t;
six scattering sheets therebelow 2 t;
one polished-aluminum sheet therebelow 1 t; and
one foamed rubber sheet therebelow 5 t, which are contained in a light-shielding black metallic case.

The scattering sheets to be used are chosen which is conventionally known as a cover of a lighting instrument or the like, and have a strong light-diffusion property even in a point light source. Since the living body is known as a strong scattering body and light cannot travel in a straight line, it is preferable to choose the material that has the same effect as the living body. The absorption sheets imitate a material absorbing light such as melanin, and are placed on the surface and the intermediate part. The scattering sheets and the light absorption sheets are combined as described above and contained in a light-shielding box to prevent outside light.

A measurement principle of oxygen saturation uses the fact that two different kinds of light are absorbed and reduced by hemoglobin in the living body. According to the Beer-Lambert law, the degree of the reduction is proportional to the amount of hemoglobin contained in the light passage. If it is assumed that the amount of oxidized hemoglobin is set as $HbO_2$ and the amount of deoxidized hemoglobin is set as HbR, oxygen saturation is represented as $(HbO_2/(HbO_2+HbR))\times 100\%$. When oxygen saturation is 50%, $HbO_2$ and HbR are equal to each other. From light absorption curves of $HbO_2$ and HbR, these two hemoglobin have the same light absorption coefficient at the wavelength of 805 nm. Oxygen saturation becomes 50% when the ratio R/IR is 1.0 on the phantom (in the Beer-Lambert law, the amounts of these two kinds of hemoglobin are evaluated to be the same if the degrees of absorbing infrared light are the same) if wavelengths interposing the wavelength of 805 nm are chosen so that there are the same light absorption coefficient on the higher side and lower side. Even when the absorption coefficients are different at the wavelengths to be used, correction is possible by multiplying a ratio between the absorption coefficients by the ratio R/IR.

Proof that Calibration is Performable by Phantom

Oxygen saturation becomes 50% if ratio between oxyhemoglobin and deoxyhemoglobin is 1.0. Since oxygen saturation is calibrated to be 50% when R/IR is 1.0 on the phantom, the light absorption coefficient for the wavelengths of near-infrared light is shown as follows:

HbO2: 770=0.150,805=0.196,870=0.248

Hb: 770=0.350,805=0.196,870=0.168

Light absorption coefficient ε=0.434K, K=absorbance.
The absorbance of each wavelength is shown as follows:

HbO2: 770=0.346,805=0.369,870=0.571

Hb: 770=0.806,805=0.369,870=0.387

The Beer-Lambert law indicates K=εcd, wherein c is concentration of solvent, d is optical length.
The absorbance at a certain wavelength is shown as follows:

$K\lambda = (rSO2 \times KHbO2 + (1-rSO2) \times KHb)cd$

The absorbance at each of the used wavelengths is calculated as follows:

$R = K770 = (rSO2 \times 0.346 + (1-rSO2) \times 0.806)cd$ $IR = K870 = (rSO2 \times 0.571 + (1-rSO2) \times 0.387)cd$ $R/IR = (0.806 - 0.46 rSO2)/(0.387 + 0.194 rSO2)$.

If R/IR=A is substituted, $A(0.387 + 0.194 rSO2) = (0.806 - 0.46 rSO2)$.

rSO2 is calculated as follows:

$rSO2 = (0.806 - 0.387A)/(0.46 + 0.194A)$.

When the rSO2 varies from 0% to 100%, the ideal values of A=R/IR are set as follows:

$rSO2 = 0\%, 0 = 0.806 - 0.387A, A = 2.083$ $rSO2 = 100\%, 0.46 + 0.194A = 0.806 - 0.387A$ $A = 0.346/0.581 = 0.596$.

In the case of rSO2=50%, the absorbance is calculated for each wavelength with rSO2=0.5.

From Kλ=(rSO2×KHbO2+(1−rSO2)×KHb) cd, K770=(0.5×0.346+0.5×0.806) cd=0.576 cd, and K870=(0.5×0.571+0.5×0.387) cd=0.479 cd are obtained.

Thereby, R/IR=A=1.2025 is obtained.

The absorbance at each of the wavelengths as the identical values in the case of rSO2=50% is as mentioned above. The absorbance R=K770 is 0.576 cd, the absorbance IR=K870 is 0.479 cd and, accordingly, the absorbance R is larger.

Thus, the measured voltage at the wavelength of 770 nm is corrected by multiplying the aforementioned ratio between the absorbance=1.2025. Thereby, the absorbance K770 of 0.479 cd and K870 of 0.479 cd are obtained, and R/IR=1:1 is completed so that correction to 50% is achieved.

By making this correction, the measured value by the actual apparatus is equal to the ideal value, which satisfies rSO2=50% at R/IR=1. If the correction is also made in the cases of 0% and 100%, each of ratios between the absorbance A=R/IR are obtained to be described below. Note that the calculating formula (identical value) of rSO2 has been described above.

$rSO2 = (0.806 - 0.387A)/(0.46 + 0.194A)$

Thus, if A for the correction is set to be 1.2025 times in the formula, (0.806−0.387×1.2025A)=0 and A=1.732 are obtained in the case of 0% of rSO2, while (0.46+0.194×1.2025A)=(0.806−0.387×1.2025A) and A=0.495 are obtained in the case of 100% of rSO2. Equations of the correction curve based on the ideal value thus corrected are obtained as follows:

$A < 1 rSO2 = 100 \times (1.495 - A)/0.99, 100\%$ to 50%, $A > 1 rSO2 = 100 \times (1.732 - A)/1.464, 50\%$ to 0%.

When the wavelength to be used is different, recalculation is conducted by assigning the numeric values of the absorption coefficient ε to the following equation since the absorption coefficient ε for the oxyhemoglobin and deoxyhemoglobin at each wavelength has been known.

Absorption coefficient ε=0.434K K:absorbance

The oxygen saturation measuring apparatus 1 and the oxygen saturation measuring sensor 2 as described above are applicable when numeric values about oxygen saturation and the amount of hemoglobin are required, using changing information of hemoglobin with near-infrared light.

Brain Protection during Operation

For example, when blood does not pass through a brain temporarily such as when stopping circulation due to a cardiac operation or blocking of the carotid artery due to brain surgery, oxygen saturation of the blood in the brain and information of the amount of blood can be obtained by attaching the oxygen saturation measuring sensor 2 onto the forehead. Accordingly, it is possible to easily grasp whether a dangerous state is caused or not, which helps brain protection and prevention of brain damage.

Cardiopulmonary Arrest <Resuscitation by AED>

If the cardiopulmonary state is caused at ambient temperature, oxygen saturation of the blood in the brain rapidly decreases, which results in loss of consciousness. In this case, there is no heartbeat as a matter of course, and thus a pulse-oximeter cannot be used. The oxygen saturation measuring sensor 2 using near-infrared light is capable of measuring oxygen saturation and HbI without problems as long as the blood exists.

For example, if cardiopulmonary resuscitation is tried by chest compression for so-called cardiac massage and thereby a heartbeat is restarted upon usage of an AED, oxygen saturation increases 40% or more and below 70%. Possibility of rehabilitation can be understood by recognizing the oxygen saturation at contact with an injured person.

Intracerebral Bleeding

In the aforementioned oxygen saturation measurement for the blood only at the deep area of brain tissues, information of intracranial bleeding is subtracted, and thus is not obtained. On the other hand, the aforementioned oxygen saturation measuring sensor 2 can reflect information of all hemoglobin existing in the optical passages where the near-infrared light passes. Normally, the blood exists only in the blood vessel. However, for example, in a subarachnoid hemorrhage or intracranial bleeding, hemoglobin pours from blood vessels, and the amount of hemoglobin in the measured optical passages is extraordinarily high only in the blood vessel. Thus, whether bleeding occurs or not is easily determined by referring the numeric value of HbI with respect to the reference by the phantom.

As described above, the oxygen saturation measuring sensor has an effect that reliability of information at parts having different depth is increased, and it is usable in general oxygen saturation measuring sensors and oxygen saturation measuring apparatus to non-invasively measure oxygen saturation in blood in a living body using near-infrared light.

The invention claimed is:

1. An oxygen saturation measuring sensor comprising:
   a pad attachable to a human body;
   a plurality of light sources comprising a light source A and a light source B arranged on the pad adjacent to and spaced apart from one another, and that irradiate near-infrared light;
   a plurality of light receiving elements comprising a light receiving element A and a light receiving element B arranged on the pad adjacent to and spaced apart from one another and correspond one to one to the plurality of light sources with reference to a common center between 1) the light sources A and B, and 2) the light receiving elements A and B, and that receive transmitted light from the corresponding plurality of light sources, wherein distances between 1) the light source A and the light source B, 2) the light source B and the light receiving element B, and 3) the light receiving element A and the light receiving element B are the same; and
   a ROM unit that stores a reference value through measuring transmitted light using a phantom in advance.

2. The oxygen saturation measuring sensor according to claim 1, wherein
   the pad includes a printed substrate having an attachment surface configured to be attached to the human body and a foamed rubber provided on a back surface side of the printed substrate, wherein a light source of the plurality of light sources and a light receiving element of the plurality of light receiving elements are arranged in a hole formed in the printed substrate such that a surface of the light source and a surface of the light receiving element have the same plane as the attachment surface.

3. The oxygen saturation measuring sensor according to claim 1, wherein
   sensor A comprises the light source A and light receiving element A and sensor B comprises the light source B and light receiving element B, and
   sensors A and B measure the information at different depths below the common center.

4. The oxygen saturation measuring sensor according to claim 3, wherein information at a depth measured by the sensor B is subtracted from information at a depth measured by the sensor A.

5. The oxygen saturation measuring sensor according to claim 4, wherein the sensors A and B each measure the information at their respective depths having a length of 70% to 80% of a distance between the light source and the light receiving element.

6. An oxygen saturation measuring apparatus comprising:
   a sensor unit; and
   a main body, wherein
   the sensor unit comprises:
      a pad attachable to a human body;
      a plurality of light sources comprising a light source A and a light source B arranged on the pad adjacent to and spaced apart from one another, and that irradiate near-infrared light;
      a plurality of light receiving elements comprising a light receiving element A and a light receiving element B arranged on the pad adjacent to and spaced apart from one another and correspond one to one to the plurality of light sources with reference to a common center between 1) the light sources A and B, and 2) the light receiving elements A and B, and that receive transmitted light from the corresponding plurality of light sources, wherein distances between 1) the light source A and the light source B, 2) the light source B and the and the light receiving element B, and 3) the light receiving element A and the light receiving element B are the same; and
      a ROM unit that stores a reference value through measuring transmitted light using a phantom in advance, and
   the main body comprises:
      an arithmetic processing unit that calculates actual absorbance on the basis of a light receiving value and a reference value regarding an amount of receiving light stored by the ROM and computes an oxygen state of a living body to comply with the Beer-Lambert law while comparing the reference value.

* * * * *